United States Patent [19]

Jupe et al.

[11] 4,381,973

[45] May 3, 1983

[54] PROCESS FOR THE PREPARATION OF PYROCATECHOL AND HYDROQUINONE

[75] Inventors: Christoph Jupe, Cologne; Helmut Waldmann, Leverkusen; Jürgen Baumert, Cologne; Günther Schümmer, Stommeln, all of Fed. Rep. of Germany

[73] Assignee: Bayer Aktiengesellschaft, Leverkusen, Fed. Rep. of Germany

[21] Appl. No.: 292,855

[22] Filed: Aug. 14, 1981

[30] Foreign Application Priority Data

Aug. 30, 1980 [DE] Fed. Rep. of Germany ....... 3032743

[51] Int. Cl.$^3$ .............................................. B01D 3/10
[52] U.S. Cl. ....................................... 203/80; 203/91; 568/752; 568/753
[58] Field of Search ...................... 568/751, 753, 752; 203/71, 73, 80, 91, 75, 77, 78, 81, 82, 84, 94

[56] References Cited

U.S. PATENT DOCUMENTS 4,308,112  12/1981  Jupe et al. ........................... 568/752

Primary Examiner—Frank Sever
Attorney, Agent, or Firm—Sprung, Horn, Kramer & Woods

[57] ABSTRACT

A process for the preparation of pyrocatechol and hydroquinone by reaction of phenol with a peroxidic hydroxylating reagent followed by working-up of the resultant reaction mixture is disclosed. The work-up procedure is carried out in a first rectification column operated under specified conditions and having specified separation stages in a rectification section and a stripping section whereby there is distilled overhead components which boil at a temperature lower than phenol. Taken off from the bottom is a mixture comprising phenol and materials of higher boiling point which are fed into a second rectification column which is also operated under very specified conditions whereby pure phenol is recovered overhead leaving a bottoms comprising phenol pyrocatechol and hydroquinone which are then processed to separate phenol from a mixture of pyrocatechol and hydroquinone.

11 Claims, No Drawings

PROCESS FOR THE PREPARATION OF PYROCATECHOL AND HYDROQUINONE

The present invention relates to a process for the preparation of pyrocatechol and hydroquinone.

Pyrocatechol and hydroquinone are industrially important organic fine chemicals which are used directly, for example in photographic developers, and also as intermediate products, for example, for dyestuffs, polymerisation inhibitors, pharmaceuticals and plant protection agents (see Kirk-Othmer, Encyclopaedia of Chemical Technology, 2nd edition, Volume 11, pages 462 to 492, particularly pages 469 and 488 (1966)).

The search for economical and simple preparation processes has led, inter alia, to a series of phenol oxidation processes, which yield pyrocatechol and hydroquinone as coupled products (see, for example, German Offenlegungsschrift Nos. 2,658,943, 2,410,742, 2,364,181, 2,658,545, 2,332,747, 1,593,968, 2,633,302, 2,064,497, 2,150,657, 2,167,040, 2,341,743, 2,407,398, 1,543,953 and 2,404,114, and Japanese Patent Application No. 54 55,530 and 54 66,629, and T. Tsuchiya, M. Andoh and J. Imamura, Nipp. Kag. Kaishi 1979, 3, pages 370 to 374).

In these processes, phenol is reacted with a peroxidic reagent, for example with hydrogen peroxide or a percarboxylic acid, which are, in most cases, dissolved in a solvent which is lower-boiling than phenol. A further characteristic of these processes consists in the fact that, to avoid over-oxidation, a deficiency of oxidizing agent, relative to the compound to be hydroxylated, is employed. This has the consequence that unreacted phenol is contained in the reaction mixture after the reaction.

In the previously mentioned literature, reference is mainly made to the usual methods, especially to distillation, extraction and crystallization, for working up the reaction mixture which is present after the hydroxylation. More exact data are largely lacking.

Detailed data for the reaction and working-up are to be found in two publications which describe industrial plants for the preparation of pyrocatechol and hydroquinone from phenol and hydrogen peroxide, namely in Jean Varagnat, Ind. Eng. Chem., Prod. Res. Dev., Volume 15, No. 3, pages 212 to 215 (1976) and P. Maggioni and F. Minisci, La Chimica et l'Industria, Volume 59, No. 4, pages 239 to 242 (1977).

In the publication by J. Varagnat, the separation of the reaction mixture by distillation in a sequence of five rectification columns is described. Phenol and further auxiliary and accompanying substances are obtained in four columns as top products and are re-used, whilst pyrocatechol and hydroquinone are separated in a fifth column, and the hydroquinone is then subjected to a crystallization.

The reaction mixture is also worked up mainly by distillation according to the process described by P. Maggioni and F. Minisci. After a stepwise evaporation in three separate evaporators connected in sequence, with progressively lower pressure down to 13 mbars, the remaining working-up of the mixture is effected in two rectification columns. In the first column, phenol is obtained for recycling, and in the second column, the products pyrocatechol and hydroquinone are obtained.

If the effort invested in the industrial working-up of reaction mixtures of phenol and peroxidic reagents for obtaining pyrocatechol and hydroquinone is considered, it can be established that, in the two previously described processes, the separation of the unreacted phenol, especially, requires a great effort.

A process for the preparation of pyrocatechol and hydroquinone by reaction of phenol with a peroxidic hydroxylating reagent and working-up of the mixture, which is present after the reaction and, if desired, after further treatment, and which contains unreacted phenol, one or several solvents which are lower boiling than phenol, pyrocatechol, hydroquinone and, if appropriate, further constituents, using continuously operated rectification apparatuses, has now been found, which is characterized in that (a) the mixture is continuously fed to a first rectification column at a point between the rectifying section and the stripping section, the rectification column having 3 to 20 separation stages in the stripping section and 5 to 20 separation stages in the rectifying section, this column is operated under a pressure between 0.02 and 5 bars, 20 to 95% by weight of the top product condensed as a liquid reflux, is recycled to the column, a top product, which contains practically all constituents of the feed mixture which boil more easily than phenol, is removed, and a bottom product is drawn off, which contains the phenol and substantially all of the more highly boiling constituents of the feed mixture and (b) the bottom product of the first rectification column is continuously fed to a second rectification column, at a point between the stripping section and the rectifying section, the second rectification column having 3 to 20 separation stages in the stripping section and 3 to 15 separation stages in the rectifying section, this column is operated under a pressure between 0.003 and 5 bars, 20 to 95% by weight of the product collecting at the head is condensed and is recycled as a liquid reflux to the top of the column, a substantially pure phenol is removed as the top product and a bottom product is drawn off, which contains, in addition to phenol, pyrocatechol, hydroquinone and which may contain further accompanying substances, and pyrocatechol and hydroquinone are isolated from the bottom product.

Mixtures to be employed in the working-up by distillation, according to the invention, can be obtained by reacting phenol with a peroxidic hydroxylating reagent, in a known manner, and, if desired, treating the mixture further.

Peroxidic hydroxylating reagents are those which contain an -O-O-(oxygen-oxygen) group, for example hydrogen peroxide or percarboxylic acids. Such reagents are employed, in general, as dilute solutions, but reactions are also known in which such reagents are employed in highly concentrated or pure form (see, for example, German Offenlegungsschrift No. 2,064,497).

The reactions are carried out, in general, to an extensive conversion of the peroxidic hydroxylating reagent. A conversion of over 99% is preferred, and a conversion of more than 99.7% is particularly preferred, so that the mixture to be employed in the working-up by distillation, according to the invention, is largely free of peroxide.

If desired, the mixture obtained from the reaction of phenol with the peroxidic hydroxylating reagent can be subjected to a further treatment before being used in the working-up by distillation, according to the invention. For example, this can consist in neutralizing acids contained in the reaction mixture, before working up the mixture further (see, for example, German Offenlegungsschrift No. 2,410,742). A further type of further treatment can consist, for example, in wholly or partly separating certain constituents, for example acid or acids, from the reaction mixture by means of extraction. Such a route is described, for example, by J. Varagnat, Ind. Eng. Chem. Prod. Res. Dev., Volume 15. No. 3, 1976, pages 212-215 (see especially page 214, left column, last paragraph) for removal of phosphoric acid and perchloric acid.

The mixtures to be employed in the working-up by distillation, according to the invention, contain phenol, one or several solvents which are lower-boiling than phenol, pyrocatechol, hydroquinone and may contain further constituents.

The content of phenol can vary within wide limits. In general, it is between 5 and 95% by weight, preferably between 20 and 90% by weight. However, it is also possible to employ mixtures with phenol contents differing from the above in the working-up by distillation, according to the invention.

In addition to the content of phenol, the ratio by weight of phenol to pyrocatechol and hydroquinone in the mixture to be employed is of importance for the economical operation of the working-up by distillation, according to the invention.

In general, the ratio by weight of phenol to dihydroxybenzenes can be, for example, between 0.8 and 50 to 1. Mixtures with as small a proportion of phenol as possible, relative to the sum of phenol, pyrocatechol and hydroquinone, are preferably employed. The lower limit of the proportion of phenol is not set by the working-up by distillation, according to the invention, but by the fact that in the hydroxylation reaction preceding the working-up by distillation, according to the invention, an excess of phenol, relative to the hydroxylating reagent, is necessary, in order to achieve an economical utilization of the phenol reacted as well as of the hydroxylating reagent employed (see, for example, German Offenlegungsschrift No. 2,407,398 and German Offenlegungsschrift No. 2,064,497).

For this reason, the ratio is not, as a rule, to fall below a ratio of 10 parts by weight of phenol to 1 part by weight of dihydroxybenzenes in the mixtures to be employed, in favour of a lower proportion of phenol. On the other hand, it is advantageous for the working-up by distillation, according to the invention, not to exceed a ratio of 35 parts by weight of phenol to 1 part by weight of dihydroxybenzenes, in the direction of a higher proportion of phenol, since the effort required for working-up is otherwise greater.

The content of solvents which are lower-boiling than phenol can likewise vary within wide limits. In general, it can be between 2 and 98% by weight, or between 5 and 60% by weight. The proportion of such solvents, which form phenol-containing azeotropic mixtures under the conditions of the working-up by distillation, according to the invention, in the mixture to be employed is to be kept so small that not all the phenol can be azeotropically distilled from the mixture.

This means, for example, in the case in which the phenol/water azeotropic mixture is obtained under normal pressure in the first column as the top product, that the quantity of water in the mixture employed is smaller than 9.86 times the quantity of phenol, since one part by weight of water carries over 0.1414 part by weight of phenol azeotropically. (See, for example, R. C. Weast, Handbook of Chemistry and Physics, Chemical Rubber Co., Cleveland, Ohio, 1977, 58th edition, page D 32, System No. 620).

The mixture to be employed is preferably so composed that no phenol-containing azeotropic mixtures occur as top products in the process according to the invention.

The solvents which are lower-boiling than phenol can have entered the mixture to be employed in various ways. For example, one solvent or several solvents can be involved.

Such solvents can, for example, have been used as solvents for the hydroxylating reagent, and can have been employed together with the latter in the reaction with the phenol.

For example, according to German Offenlegungsschrift 2,364,181, acetone, ethyl acetate and mixtures of acetone and methyl acetate can be used as solvents for various percarboxylic acids.

However, solvents which are lower-boiling than phenol can also, for example, be formed as by-products from the hydroxylating reagent. Thus, for example, the hydroxylation with hydrogen peroxide yields an equivalent quantity of water according to the following equation:

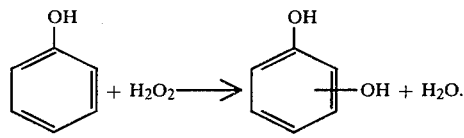

A hydroxylation with peracetic acid, for example, yields the quantity of acetic acid equivalent to the quantity of reacted peracetic acid, according to the following equation:

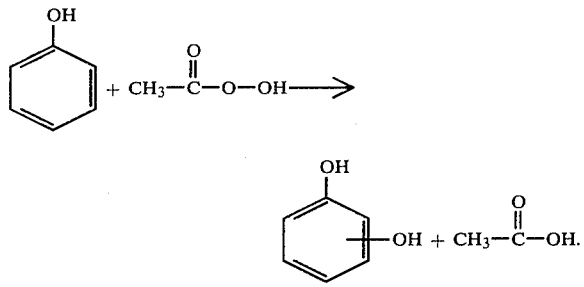

Solvents, for example hydrocarbons or chlorinated hydrocarbons, can be used as part of the reaction medium of the hydroxylation reaction, so that, for example, solvents which are lower-boiling than phenol can also have been introduced in this way into the mixture to be employed.

A further treatment, which is carried out, if desired, between the hydroxylation reaction and the working-up by distillation, according to the invention, can also lead to the presence in the mixture to be employed of solvents which are lower-boiling than phenol. Thus, for example, in the process described by J. Varagnat (see J. Varagnat Ind. Eng. Chem. Prod. Res. Dev. Vol. 15, No. 3, pages 212-215 (1976)), diisopropyl ether is added to the reaction mixture of the hydroxylation in order to achieve a good phase separation on extraction of the mixture with water.

Mixtures with as small a quantity as possible of solvents which are more easily boiling than phenol are preferably employed in the working-up by distillation, according to the invention. In general, the minimum content is not determined by the working-up by distillation, according to the invention, but by preceding process stages. For example, it is industrially customary to use hydrogen peroxide as 30, 50 or 70% by weight strength aqueous solution, since more highly concentrated aqueous solutions of hydrogen peroxide, from about 85% by weight, are capable of detonation. Consequently, water which has formed from hydrogen peroxide during the reaction with phenol, as well as water which has been introduced into the reaction together with the hydrogen peroxide, are present in a reaction mixture of this kind.

In general, it is not decisive for the working-up by distillation, according to the invention, of which chemical substances the solvent or the solvents which are lower-boiling than phenol consist. The term "solvent" is to be understood here as meaning that, under the conditions of the working-up by distillation, according to the invention, the constituents of the mixture to be employed which are thus characterized preferably do not react or only react in part with themselves, among one another or with other constituents of the mixture to be employed. It is desirable that as small an amount as possible of solvents which are lower-boiling than phenol be consumed by reactions during the working-up by distillation, according to the invention.

In general, up to 80% of the proportion of one or several solvents of the mixture to be employed can be consumed by reactions of the solvent or the solvents during the working-up by distillation, according to the invention. Of course, it is preferable to consume by reactions at most 10%, very particularly preferably under 5%, of one or several solvents of the mixture to be employed.

The following may be mentioned as examples of solvents which boil at a lower temperature than phenol and which can be present, in the mixture to be employed, alone or in mixtures: water, 1,2-dichloropropane, acetic acid, methyl acetate, ethyl acetate, acetone, diisopropyl ether, propionic acid, isobutyric acid, benzene, toluene, o-xylene, m-xylene, p-xylene, dioxane, 1,2-dichloroethane and 1,1,2-trichloroethane.

The mixtures to be employed in the working-up by distillation, according to the invention, contain the dihydroxybenzenes pyrocatechol and hydroquinone. The content of these substances can vary within wide limits. This is likewise the case for the ratio of pyrocatechol to hydroquinone.

In general, the content of dihydroxybenzenes is between 0.1 and 95% by weight. Although as large a content as possible of dihydroxybenzenes is preferred, in many cases a content of below 60% by weight of dihydroxybenzenes is present in the mixture to be employed, owing to the unreacted phenol present after the reaction and because of the solvent or solvents which are more easily-boiling than phenol. The content of dihydroxybenzenes in the mixture to be employed is frequently between 0.5 and 10% by weight.

The ratio by weight of pyrocatechol to hydroquinone is not of importance for the process according to the invention. In general, this ratio is between 0.1 and 10 or between 0.8 and 4.

The mixtures to be employed in the working-up by distillation, according to the invention, can contain, in addition to the constituents hitherto listed and described, one or several further constituents.

The content of further constituents can vary within wide limits, and can, for example, be between 0.1 and 50% by weight. As small a content as possible of further constituents is preferred.

The optionally present further constituents can have boiling points which are above or below the boiling point of phenol. They can also be very high-boiling or non-distillable.

If further constituents wholly or partly form phenol-containing azeotropic mixtures, which may also contain other, already-mentioned constituents of the mixture to be employed, under the conditions of the working-up by distillation, according to the invention, their proportion in the mixture to be employed is to be kept so small that not all the phenol can be azeotropically distilled off from the mixture.

In general, the further constituents have the same chemical properties as the already-mentioned solvents which are lower-boiling than phenol. That is to say, they are chemically largely or at least sufficiently inert under the conditions of the working-up by distillation, according to the invention.

Mixtures are preferably employed in the working-up by distillation, according to the invention, which, if they contain further constituents in the above sense, only contain those further constituents which have boiling points either lower than the boiling point of the phenol or higher than the boiling point of the pyrocatechol. Those mixtures are therefore preferred in which no substances which boil between phenol and pyrocatechol are contained. Mixtures which, if they contain further constituents in the above sense, only contain those further substituents which have boiling points either lower than the boiling point of the lowest-boiling solvent or of the lowest-boiling solvent mixture and/or higher than the boiling point of the pyrocatechol are very particularly preferred.

In addition, it is of very particular advantage for the separation of pyrocatechol and hydroquinone by distillation only to employ those mixtures in the working-up by distillation, according to the invention, which, thus they contain further constituents in the above sense, only contain those further constituents which either boil lower than the lowest-boiling solvent or solvent mixture and/or which boil higher than hydroquinone and/or which are non-distillable under the conditions of the working-up by distillation, according to the invention.

The optionally present further constituents can have entered the mixture to be employed in various ways. They can be chemically of the most variable nature and can be, in part, of a nature which cannot even exactly be determined chemically.

The following may be mentioned as examples of further constituents:

oxygen, which can originate, for example, from the decomposition of a peroxidic reagent;

carbon oxides ($CO$, $CO_2$), which can have been formed, for example, by over-oxidation in the hydroxylation reaction;

salts of acids, which can have been formed, for example, in the neutralization of acids in the reaction mixture;

trihydroxybenzenes, which can have been formed, for example, in the hydroxylation reaction as by-products;

organic substances which are higher-boiling than hydroquinone or which are non-distillable, which, for example, can behave similarly to lignites or to humic acids or can have a tar-like behaviour, and which can have been formed, for example, as by-products of the hydroxylation reaction;

phosphorus-containing substances which are higher-boiling than hydroquinone or which are non-distillable, or other substances which are higher-boiling than hydroquinone and which have metal-complexing properties, which, for example, can have been added to the hydroxylation mixture or which can have been formed from added complex-forming substances.

For example, mixtures which have been obtained by reaction of phenol with the solution of a monopercarboxylic acid with 2 to 4 carbon atoms, in an organic solvent with a boiling point above 100° C. (under normal pressure), are well suited for the working-up by distillation, according to the invention. Such mixtures can contain the solvent, the carboxylic acid corresponding to the percarboxylic acid, and up to 5% by weight of water, as constituents which are lower-boiling than phenol. Particularly suitable mixtures are those which contain benzene, propionic acid and up to 5% by weight of water, as constituents which are lower-boiling than phenol.

For the operation of the working-up by distillation, according to the invention, the starting mixture is continuously fed to a first rectification column, between rectifying section and stripping section.

This column has 3 to 20 separation stages in the stripping section and 5 to 20 separation stages in the rectifying section.

5 to 18 separation stages are preferred, and 9 to 16 separation stages are very particularly preferred, in the stripping section. 5 to 18 separation stages are preferred for the rectifying section, and 7 to 16 separation stages are particularly preferred for this section.

In the above and in the text which follows, a separation stage is defined as a column section, the separating action of which, in a rectification, is capable of establishing the equilibrium between ascending vapour phase and descending liquid phase, as is explained, for example, in "Organikum, Organisch-Chemisches Grundpraktikum" ("Organic Chemistry, Fundamental Practical Principles"), 15th edition (reprinting), VEB Deutscher Verlag der Wissenschaften, Berlin 1977, pages 63–69, especially pages 66 and 67.

This column is operated at a pressure between 0.02 and 5 bars. The column is preferably operated at a pressure between 0.1 to 1.2 bars. An operational pressure of between 0.2 and 1.1 bars is very particularly preferred.

The temperatures in the column are established according to the pressure and the composition of the substance mixtures at the various points of the column. The whole working-up by distillation, according to the invention, is advantageously operated in such a manner that a temperature of 250° C. is not exceeded at the product end. Temperatures between 230° and 250° C. at the product end are preferably to be reached at most for a short time. It is very particularly preferred always to have temperatures at the product end of below 230° C.

The lower limit for temperature or pressure is set by the solidification point of the top product. The boiling temperature determined by pressure and composition of the top product must be above the melting point of the top product, otherwise a rectification yielding a liquid reflux consisting of condensed top product cannot be carried out.

A part of the vapour produced at the head of the column is condensed and returned to the column in liquid form as the so-called "reflux". The part of the top product which is not returned to the column as a reflux is withdrawn (so-called "withdrawal"). In general, the ratio by weight of reflux to withdrawal (R:W) is between 0.25 and 19. A ratio R:W of between 0.5 and 10 is preferred. A ratio R:W of between 0.8 and 5 is very particularly preferred.

A top product is withdrawn which contains practically all of the constituents of the mixture employed, which are lower-boiling than phenol. That is to say, the column is operated with such a supply of energy that only small amounts of constituents which are lower-boiling than phenol are still contained in the bottom product.

The content of constituents, which are lower-boiling than phenol, in the bottom product can be between 0.005 and 2% by weight. Within this range, as low a content as possible of constituents which are lower-boiling than phenol is preferred.

The content in the top product of phenol and components which are higher-boiling than phenol is small. It can be between 0.005 and 5% by weight. A phenol content of 0.5 to 2% by weight is preferred.

The withdrawn top product can be put to any desired use. If the top product contains more than one substance, it can be subjected, for example, to a further separation, in order to obtain the individual substances as pure materials.

It is preferable to obtain solvents pure and to re-use them, for example as solvents for peroxidic hydroxylation reagents. Likewise, it is often advantageous to recover in pure form a solvent formed from a peroxidic hydroxylating agent, for example isobutyric acid formed from perisobutyric acid, and to employ it again for the preparation of the corresponding peroxidic compound (in the example given: perisobutyric acid).

The bottom product obtained from the first rectification column of the working-up by distillation, according to the invention, is continuously fed to a second rectification column, between stripping section and rectifying section. The second rectification column has 3 to 20 separation stages in the rectifying section and 3 to 15 separation stages in the stripping section.

A column with 4 to 10 separation stages in the rectifying section and 4 to 8 separation stages in the stripping section is preferably to be employed as the second rectification column, and 5 to 7 separation stages in the rectifying section and 5 to 6 separation stages in the stripping section are very particularly preferable.

The second rectification column is operated at a pressure of between 0.003 and 5 bars, preferably between 0.01 and 1.2 bars and very particularly preferably between 0.02 and 0.8 bar.

The top product is a largely pure phenol with a phenol content of above 95% by weight. A top product with above 99% by weight of phenol is preferably obtained, and a top product with above 99.8% by weight of phenol is very particularly preferably obtained.

The top product is partly condensed and is returned in liquid form as a reflux to the top of the rectification column.

The proportion which is returned to the column as a reflux is between 20% and 95% of the total product produced at the head. 50 to 75% of the product produced at the head is preferably used as a reflux. This corresponds to a ratio of reflux to withdrawal (R:W) of between 1:1 and 3:1. 55% to 65% of the product produced at the head is particularly preferably used as a reflux.

The part of the top product which is not used as a reflux is withdrawn and can be used as desired. In general, it is condensed and is further used in liquid or solid form.

The phenol withdrawn as a top product, if appropriate after further purification or other treatment, is preferably employed again in the reaction with the hydroxylating reagent.

It is particularly preferable to use the top product of the first as well as the top product of the second rectification column completely or partly in the process for the preparation of pyrocatechol and hydroquinone and/or one of its preliminary stages.

In general, the largest part of the phenol quantity which is in the feed is withdrawn as a top product of the second rectification column. A quantity of phenol is preferably withdrawn at the head so that a content of 30 to 70% by weight of phenol is present in the bottom product.

A phenol content of 40 to 65% by weight is particularly preferably present in the bottom product.

A bottom product is withdrawn, which contains the phenol, pyrocatechol, hydroquinone and other constituents which are higher-boiling than phenol.

Pyrocatechol and hydroquinone are isolated from this bottom product. This can be effected in the customary manner, for example by distillation, extraction, rectification and/or crystallisation. A particularly suitable process is described, for example, in U.S. application Ser. No. 166,270, filed July 2, 1980, entitled "Process for the Isolation of Pyrocatechol and Hydroquinone", assigned to the assignee hereof, the disclosure of which is hereby incorporated herein by reference. According to that process the pyrocatechol and hydroquinone are separated from one another by rectification to obtain pyrocatechol as overhead followed by evaporation of hydroquinone from the rectification bottoms.

All customary rectification columns, such as, for example, packed columns or tray columns, are suitable for the operation of the working-up by distillation, according to the invention. Columns with fabric or other packings are also well suited. Likewise, the type of evaporator which belongs to the column is not decisive for the operation of the working-up according to the invention, since all customary evaporator types can be employed, such as, for example, tubular heat exchangers or falling film evaporators with forced circulation.

All industrially customary materials, which are sufficiently stable to the substances to be separated, in the temperature range up to about 250° C., can be employed for the manufacture of the rectification apparatuses. Glass, titanium and high-alloy refined steels with chromium and/or nickel contents of above 10% by weight in each case, for example materials according to DIN (German Industrial Standards) 1.4571 or DIN (German Industrial Standards) 1.4439, or V4A stainless steel, are examples of suitable materials.

An advantageous form of operation of the working-up by distillation according to the invention is represented in the following:

The mixture to be employed is obtained by reaction of phenol with the solution of a percarboxylic acid having 2 to 4 carbon atoms, in an organic solvent, and contains: 8–15 parts by weight of an organic solvent which boils below 100° C., such as benzene, 1,2-dichloropropane or ethyl acetate, 0.5–2 parts by weight of water, 3–8 parts by weight of a monocarboxylic acid with 2 to 4 carbon atoms, 50–90 parts by weight of phenol, 1.5–4 parts by weight of pyrocatechol, 0.6–3 parts by weight of hydroquinone, 0.2–2 parts by weight of high-boiling constituents (2 to 4% by weight thereof inorganic salts, the remainder of organic nature with a ratio of 60 to 80 parts by weight of carbon, 15 to 25 parts by weight of oxygen and 2 to 8 parts by weight of hydrogen).

The mixture is fed, between stripping section and rectifying section, to a packed rectification column or sieve tray rectification column of glass or V4A stainless steel, which has 4 to 8 theoretical separation stages in the rectifying section and 4 to 8 theoretical separation stages in the stripping section.

The column is operated at a head pressure of 200 to 1,100 mbars. The ratio of reflux to withdrawal is between 0.5:1 and 8:1.

The top product contains practically the total amount of solvent, water and carboxylic acid. The phenol content in the top product is below 0.01% by weight. The top product is separated in a further rectification column into a top product of the organic solvent and water, and a bottom product of the carboxylic acid and a trace of phenol. Both products are employed again for the preparation of the solution of the percarboxylic acid.

The bottom product, which contains less than 0.1% by weight of constituents which are lower-boiling than phenol, is fed to a second rectification column, between rectifying section and stripping section. This second rectification column has 3 to 5 separation stages in the stripping section as well as in the rectifying section, and is operated at a head pressure of from 20 to 800 mbars. The ratio of reflux to withdrawal is between 1.1:1 and 4:1.

The principal amount of the phenol in the feed to the second column is withdrawn at the head as pure phenol, which contains less than 0.3% by weight of constituents which are lower-boiling than phenol and less than 0.01% by weight of constituents which are higher-boiling than phenol, and is fed to the hydroxylation reaction.

The bottom product, which contains about 50% by weight of phenol, pyrocatechol, hydroquinone and higher-boiling constituents, is withdrawn, and is subjected to a further working-up for the recovery of pyrocatechol and hydroquinone, for example according to the process described in the U.S. application Ser. No. 166,270.

The effort is reduced in comparison to the known processes for the separation of these or similar mixtures. The working-up by distillation, according to the invention, has, in addition, the advantage that the high-boiling constituents occuring in the process, which are, in general, high-boiling oxidation products of the phenol, remain dissolved and are deposited neither in the evaporators, nor in the bottom product, nor elsewhere in the columns, so that blockages are avoided and deposits remain limited to a very small extent.

It is to be regarded as surprising that, with a process which is simpler in comparison to known processes, a phenol can be obtained as the top product, which can be employed again in the hydroxylation reaction without complicated measures. The specialist would have rather expected, with a knowledge of the known processes, that an improved operation of the process would only be possible with an increased investment in apparatus and energy.

EXAMPLE:

The example which follows is intended to illustrate the invention in more detail, without in any way limiting it.

1.09 kg/h of a mixture, which was obtained by reaction of phenol with a solution of perpropionic acid in a mixture of benzene and propionic acid, was continuously fed to the middle of a rectification column.

The following components were determined in the mixture fed to the column

| benzene | 11.47% by weight |
|---|---|
| propionic acid | 6.50% by weight |
| water | 0.25% by weight |
| phenol | 77.30% by weight |
| pyrocatechol | 2.48% by weight |
| hydroquinone | 1.56% by weight |

The undetermined remainder of 0.45% by weight consisted of various substances, which boiled at a higher temperature than hydroquinone or which did not boil without decomposing.

The rectification column was of glass and had an active length of 3,000 mm. It was filled with glass Raschig rings of the dimensions 4×4 mm, and the internal column diameter was 50 mm.

Before entry into the column, the mixture was heated to 90° C. in a glass heat exchanger, which was heated with thermal oil.

The column was maintained under a pressure of 250 mbars (measured at the head of the column).

An evaporator with convection circulation, likewise made of glass, was situated at the bottom product, and was heated with thermal oil at 200° C. A temperature of 142°-143° C. was established in the bottom product, and 73°-82° C. was measured at the head. A quantity of 1.4 kg of product per hour was produced as a distillate at the head of the column.

The top product was condensed, 1.2 kg/h was returned as a liquid reflux to the head of the column, and 0.2 kg/h was withdrawn.

The top product had the following composition:

| benzene | 62.5% by weight |
|---|---|
| propionic acid | 35.0% by weight |
| water | 1.33% by weight |
| phenol | 1.17% by weight |
| | 100.00% by weight |

Benzene and propionic acid were isolated from the withdrawn top product, and were employed in the preparation of a solution of perpropionic acid in benzene/propionic acid.

0.89 kg/h of product was withdrawn from the bottom product of the column and was fed to the middle of a second rectification column.

The following constituents were analysed in the bottom product withdrawn:

| propionic acid | 0.09% by weight |
|---|---|
| phenol | 94.42% by weight |
| pyrocatechol | 3.03% by weight |
| hydroquinone | 1.91% by weight |
| | 99.45% by weight |

The second rectification column had the following dimensions: active length 2,400 mm, internal diameter 50 mm, packing: 4×4 mm glass Raschig rings; material for column and evaporator: glass.

Before entry into the column, the mixture was heated to 140° C.

The column was operated under a pressure of 667 mbars, measured at the head of the column. The temperatures were 181° to 182° C. in the bottom product, and 166° to 167° C. in the head.

The column was provided with an evaporator with a convection circulation, which was heated with thermal oil of 230° C.

A quantity of 1.89 kg/h of product was produced at the head of the column, and this product was condensed.

1.13 kg/h of the top product was returned to the column in liquid form as a reflux.

The following substances were analysed in the top product:

| propionic acid | 0.08% by weight | |
|---|---|---|
| phenol | 99.92% by weight | |
| pyrocatechol | a trace | below 0.01% by |
| hydroquinone | a trace | weight in each case |

The top product was employed for the reaction with perpropionic acid.

0.13 kg of product per hour was withdrawn from the bottom product of the second rectification column, and the following constituents were analytically detected in this product.

| phenol | 62.23% by weight |
|---|---|
| pyrocatechol | 20.62% by weight |
| hydroquinone | 13.00% by weight |

Phenol, pyrocatechol and hydroquinone were isolated from the bottom product by means of further rectifications. The phenol was employed for the reaction with perpropionic acid.

What is claimed is:

1. In a process for the preparation of pyrocatechol and hydroquinone by reaction of phenol with a peroxidic hydroxylating reagent followed by working-up of the mixture, which is present after the reaction, and which contains unreacted phenol, at least one solvent which is lower boiling than phenol, pyrocatechol and hydroquinone, using continuously operated rectification apparatuses, the improvement wherein:

(a) the mixture is continuously fed to a first rectification column at a point between the recitifying section and the stripping section, the rectification column having 3 to 20 separation stages in the stripping section and 5 to 20 separation stages in the rectifying section, this column operated under a pressure between 0.02 and 5 bars, 20 to 95% by weight of the top product condensed as a liquid reflux, is recycled to the column, a top product, which contains practically all constituents of the feed mixture which boil more easily than phenol, is removed, and a bottom product is drawn off, which contains the phenol and practically all of the more highly boiling constituents of the feed mixture; and (b) the bottom product of the first rectification column is continuously fed to a second rectification column, at a point between the stripping section and the rectifying section, the second rectification column having 3 to 20 separation stages in the stripping section and 3 to 15 separation stages in the rectifying column, this column is operated under a pressure between 0.003 and 5 bars, 20 to 95% by weight of the product collecting at the head is condensed and is recycled as a liquid reflux to the top of the column, a pure phenol product containing less than 0.3% by weight of constituents which are lower boiling than phenol and less than 0.01% by weight of constituents which are higher boiling than phenol is removed as the top product and a bottom product is drawn off, which contains in addition to phenol, pyrocatechol and hydroquinone, and pyrocatechol and hydroquinone are isolated from the bottom product.

2. A process according to claim 1, wherein the mixture to be rectified contains the following proportions:

| | |
|---|---|
| solvents boiling below 100° C. | 8 to 15 parts by weight |
| water | 0.5 to 2 parts by weight |
| monocarboxylic acid with 2 to 4 C atoms | 3 to 8 parts by weight |
| phenol | 50 to 90 parts by weight |
| pyrocatechol | 1.5 to 4 parts by weight |
| hydroquinone | 0.6 to 3 parts by weight |
| high-boiling solvents | 0.2 to 2 parts by weight |

3. A process according to claim 1, wherein an organic solvent with a boiling point below 100° C. (at normal pressure), as the solvent which is lower-boiling than phenol, a monocarboxylic acid with 2 to 4 C atoms, and up to 5% by weight of water are contained in the mixture to be rectified.

4. A process according to claim 3, wherein said mixture contains benzene, propionic acid and up to 5% by weight of water.

5. A process according to claim 1, wherein a temperature of 230° C. at the product end is not exceeded.

6. A process according to claim 1, wherein the first rectification column is operated at a head pressure of between 0.1 and 1.2 bar and the second rectification column is operated at a head pressure of between 0.02 and 0.8 bar.

7. A process according to claim 1, wherein a product which contains over 99% by weight of phenol is obtained as the top product of the second rectification column.

8. A process according to claim 1, wherein the first rectification column is operated at a reflux ratio R:W (reflux:withdrawal) of between 0.5:1 and 10:1 (parts by weight) and the second rectification column is operated at a reflux ratio R:W of between 1:1 and 3:1.

9. A process according to claim 1, wherein the first rectification column has
5 to 18 separation stages in the rectifying section and
5 to 18 separation stages in the stripping section, and
the second rectification column has
4 to 10 separation stages in the rectifying section and
4 to 8 separation stages in the stripping section.

10. A process according to claim 1, wherein the top products of the first and second rectification columns are wholly or partly re-used in the process for the preparation of pyrocatechol and hydroquinone, and/or in one of its preliminary stages.

11. In a process for the preparation of pyrocatechol and hydroquinone by reaction of phenol with a peroxidic hydroxylating reagent followed by working-up of the mixture, which is present after the reaction, and which contains unreacted phenol, at least one solvent which is lower boiling than phenol, pyrocatechol and hydroquinone, and which is subjected to a further treatment, using for the working-up continuously operated rectification apparatuses, the improvement wherein (a) the mixture is continuously fed to a first rectification column at a point between the rectifying section and the stripping section, the rectification column having 3 to 20 separation stages in the stripping section and 5 to 20 separation stages in the rectifying section, this column is operated under a pressure between 0.02 and 5 bars, 20 to 95% by weight of the top product condensed as a liquid reflux, is recycled to the column, a top product, which contains practically all constituents of the feed mixture which boil more easily than phenol, is removed, and a bottom product is drawn off, which contains the phenol and practically all of the more highly boiling constituents of the feed mixture; and (b) the bottom product of the first rectification column is continuously fed to a second rectification column, at a point between the stripping section and the rectifying section, the second rectification column having 3 to 20 separation stages in the stripping section and 3 to 15 separation stages in the rectifying section, this column is operated under a pressure between 0.003 and 5 bars, 20 to 95% by weight of the product collecting at the head is condensed and is recycled as a liquid reflux to the top of the column, a pure phenol product containing less than 0.3% by weight of constituents which are lower boiling than phenol and less than 0.01% by weight of constituent which are higher boiling than phenol is removed as the top product and a bottom product is drawn off, which contains in addition to phenol, pyrocatechol and hydroquinone, and phyrocatechol and hydroquinone are isolated from the bottom product.

* * * * *